(12) United States Patent
Dehli

(10) Patent No.: US 6,786,878 B2
(45) Date of Patent: Sep. 7, 2004

(54) WARM AIR MASSAGER

(75) Inventor: Hans Dehli, Dana Point, CA (US)

(73) Assignee: Interactive Health, LLC, Long Beach, CA (US)

( * ) Notice: Subject to any disclaimer, the term of this patent is extended or adjusted under 35 U.S.C. 154(b) by 0 days.

(21) Appl. No.: 09/880,411

(22) Filed: Jun. 11, 2001

(65) Prior Publication Data

US 2002/0072693 A1 Jun. 13, 2002

Related U.S. Application Data

(60) Provisional application No. 60/210,514, filed on Jun. 9, 2000, provisional application No. 60/266,578, filed on Feb. 5, 2001, and provisional application No. 60/293,719, filed on May 25, 2001.

(51) Int. Cl.[7] .............................................. A61H 23/02
(52) U.S. Cl. ........................... 601/16; 601/70; 601/80
(58) Field of Search ............................. 601/15, 18, 89, 601/93, 94, 95, 97, 101, 107, 108, 110, 111, 26, 70, 80; 607/96

(56) References Cited

U.S. PATENT DOCUMENTS

| 1,951,776 | A | | 3/1934 | Shelton |
| 3,489,138 | A | * | 1/1970 | Lifschitz .................... 601/18 |
| 4,196,343 | A | * | 4/1980 | Han ........................... 392/385 |
| 4,596,565 | A | * | 6/1986 | Ruderian .................... 604/291 |
| 4,597,757 | A | | 7/1986 | Ruderian |
| 4,763,657 | A | * | 8/1988 | Chen et al. ................. 607/96 |
| 5,101,809 | A | * | 4/1992 | Daffer et al. ............... 601/52 |
| 5,159,922 | A | * | 11/1992 | Mabuchi et al. ........... 601/110 |
| 5,526,578 | A | * | 6/1996 | Iyer ............................. 34/97 |
| 5,716,332 | A | * | 2/1998 | Noble ........................ 601/108 |
| 6,183,427 | B1 | * | 2/2001 | Ishii ........................... 601/46 |

FOREIGN PATENT DOCUMENTS

| DE | 19 39 936 A | | 2/1971 |
| WO | WO 86/04809 | | 8/1986 |
| WO | WO 92/14435 | * | 9/1992 |

OTHER PUBLICATIONS

International Search Report, dated Oct. 4, 2002, for International Application No. PCT/US 01/40949; filed Jun. 11, 2001.

* cited by examiner

Primary Examiner—Jerome W. Donnelly
(74) Attorney, Agent, or Firm—Christie, Parker & Hale, LLP

(57) ABSTRACT

A warm air massager for heating and massaging a body part includes a massage node which includes openings for directing streams of heated air to the body part being massaged. The body part is massaged by the reciprocating motion of the massage node produced by an internal massage motor. The massage motor may rotate to cause an eccentric connector to impart reciprocating motion to a shaft coupled to the massage node. The massage motor may be located within the housing, within the massage node, or there may be multiple massage motors located in each of the housing and the massage node. Intake ambient air enters the massage housing by means of a fan which withdraws ambient air from outside, directs the ambient air through a heater element and directs streams of the heated air through the massage node to the body part being massaged. Each of the fan, the heater element and the massage motor or motors may include multiple settings. The fan and massage motor are preferably separately controlled.

35 Claims, 3 Drawing Sheets

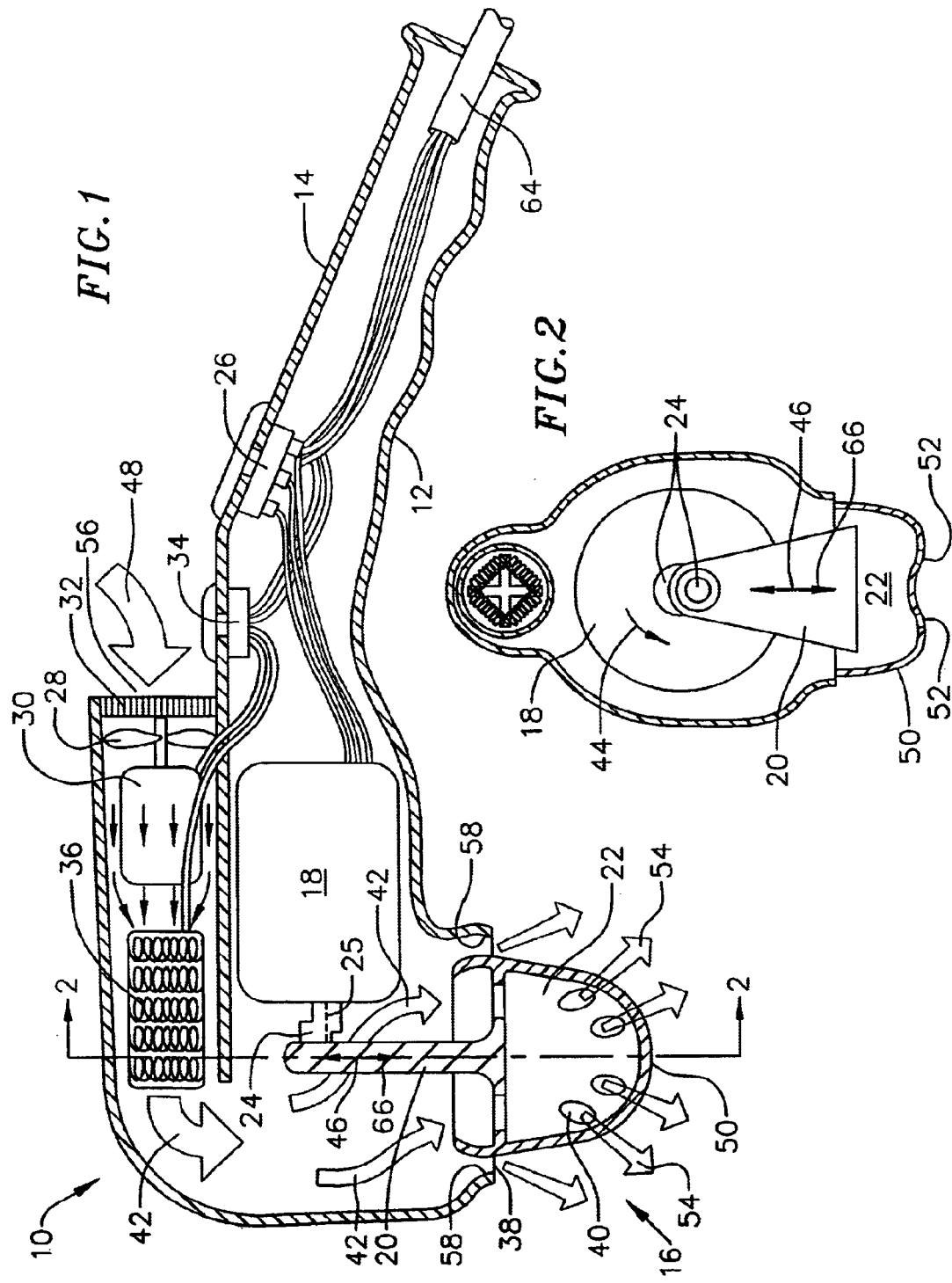

WARM AIR MASSAGER

CROSS-REFERENCE TO RELATED APPLICATIONS

This application claims priority of U.S. Provisional Application Serial No. 60/210,514 filed Jun. 9, 2000; U.S. Provisional Application Serial No. 60/266,578 filed Feb. 5, 2001; and U.S. Provisional Application Serial No. 60/293,719 filed May 25, 2001.

FIELD OF THE INVENTION

The present invention is related most generally to massaging devices and more particularly, to massaging devices that provide heated air to the body part being massaged.

BACKGROUND OF THE INVENTION

It is desirable to massage a body part to soothe the body part and to relieve stress and tightness by providing a comfortable stimulation. Various massaging methods and devices are known in the art. Effective massaging methods include vibration of a massage node and reciprocation of a massage node to repeatedly impact the body part being massaged in a rapid succession of small strokes. It is also generally comfortable and soothing to have a diffused stream of moderately heated air directed onto body parts, particularly those being simultaneously massaged.

The present invention is directed to providing a massaging device which both massages a user's body part and provides a diffused stream of heated air directly to the body part being massaged.

SUMMARY OF THE INVENTION

The present invention provides a warm air massager for heating and massaging a body part. The warm air massager includes a massage motor which provides motion to a massage node which massages the user's body part. Ambient air is heated and this heated air is directly provided to the body part being massaged through at least one opening preferably formed in the massage node.

Another aspect of the present invention is a warm air massager including a housing and a massage node including a convex massaging surface and extending from an orifice formed in the housing. A motor positioned within the massage node is capable of causing the massage node to reciprocate or vibrate or both.

Still another aspect of the present invention is a method for massaging a body part. The method includes providing a massage node, causing the massage node to reciprocate, and directing at least one stream of heated air through an opening formed in the massage node and towards the body part.

It is to be understood that the foregoing general description and the following detailed description are exemplary, but not restrictive of the invention.

BRIEF DESCRIPTION OF THE DRAWING

The invention is best understood from the following detailed description when read in connection with the accompanying drawing. It is emphasized that, according to common practice, the various features of the drawing are not-to-scale. On the contrary, the dimensions of the various features are arbitrarily expanded or reduced for clarity. Included in the drawing are the following figures:

FIG. 1 is a cross-sectional side view of an exemplary embodiment of the warm air massager of the present invention;

FIG. 2 is a cross-sectional front view taken along line 2—2 of FIG. 1;

Like numerals denote like features throughout the specification and figures.

DETAILED DESCRIPTION

Figure 3:
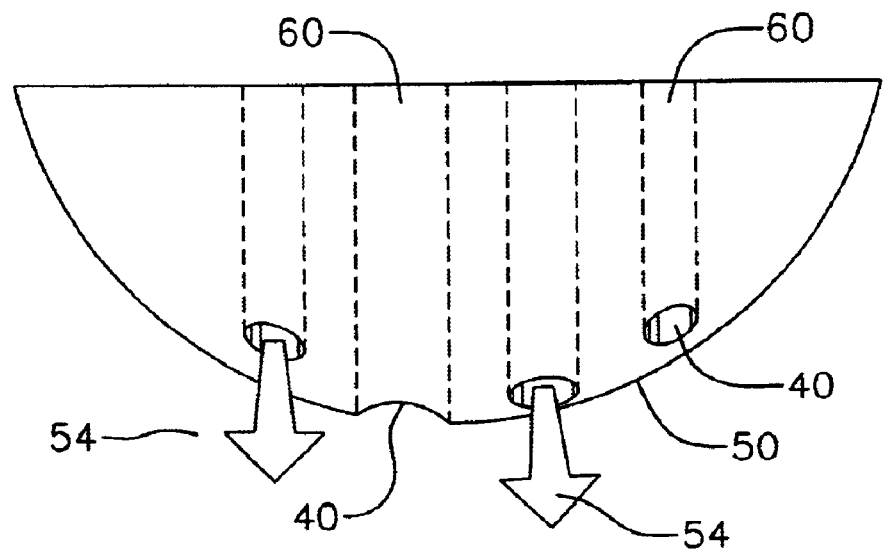
FIG. 3 is a cross-sectional side view of an exemplary embodiment of the massage node having openings therethrough and which includes outlet ports for directing heated air streams to the body part.

The present invention may be used to massage a body part with a massage node and to provide a soothing stream of moderately heated air through the massage node and to the body part being massaged. The body part is advantageously massaged by a reciprocating motion of the massage node which repeatedly impacts the body part being massaged in a rapid succession of short strokes. According to another exemplary embodiment, the massage node may vibrate to provide the massaging action. In a preferred embodiment, the warm air massager of the present invention is a handheld unit and includes a housing. A massage motor is contained within the housing, the massage node, or both. In an exemplary embodiment, ambient air is withdrawn into the housing by means of a fan, heated by passing through a heating element, then expelled and directed to the body part.

FIG. 1 shows a cross-sectional view of an exemplary embodiment of the warm air massager of the present invention. In the exemplary embodiment of FIG. 1, warm air massager 10 is a hand-held unit including handle portion 14 and massaging portion 16. According to other exemplary embodiments, the warm air massager may take on various other configurations. Within massaging portion 16, massage node 22 is fixedly attached to shaft 20. Shaft 20 reciprocates along reciprocating direction 46. Massage node 22 is situated within, and extends from, orifice 58 of housing 12. Housing 12 may be formed of conventional materials such as plastic or other polymeric materials. It should be understood that housing 12 and orifice 58 are exemplary only and that various other configurations of housing 12 may be used. Orifice 58 and therefore massage node 22 may be positioned variously within housing 12.

When translating up and down along the opposed directions indicated by the arrowheads of reciprocating direction 46, massage node 22 travels within orifice 58 of housing 12 as it extends from housing 12 for massaging a user's body part (not shown). Shaft 20 may be formed of suitable rigid conventional materials such as aluminum, titanium, or other metals, polymers or plastics. Massage node 22 may be formed of plastics, rubber, or other suitable conventional materials. Massage node 22 includes massage surface 50 which impacts the body part being massaged and may be formed of various plastics, rubber, or other suitable smooth materials conventionally used for massaging a body part. In an exemplary embodiment, massage surface 50 forms the entire surface of massage node 22.

Shaft 20 and therefore massage node 22 reciprocate along reciprocating direction 46 which is an axial direction with respect to shaft 20. This axial motion is produced in response to rotational motion of massage motor 18. Massage motor 18 is coupled to shaft 20 by means of eccentric connector 24.

Eccentric connector 24 is made to rotate about rotation axis 25 due to rotational motion provided by massage motor 18. The conversion of rotational motion to axial motion by means of eccentric connector 24 is also shown in FIG. 2. Eccentric connector 24 is shaped and positioned to enable the rotational motion of massage motor 18 to produce short strokes in the reciprocating motion of shaft 20 as it axially reciprocates along reciprocating direction 46.

FIG. 2 is a cross-sectional front view taken along line 2—2 of FIG. 1. Massage motor 18 provides rotational motion 44. Rotational motion 44 may be counter-clockwise, as shown, or it may be clockwise. Massage motor 18 may be any of various suitable conventional motors for providing rotational motion and may be an electrical motor in the preferred embodiment. Rotational motion 44 provided by massage motor 18 is converted into reciprocating motion of shaft 20 along reciprocating direction 46 which is a generally axial motion with respect to shaft 20. In an exemplary embodiment, shaft 20 alternatively moves along the opposed directions indicated by the arrowheads of reciprocating direction 46. Included in this motion is massaging direction 66. Massage node 22 moves along massaging direction 66 towards the body part being massaged (not shown). In an exemplary embodiment, massage motor 18 and eccentric connector 24 are arranged and the rotational speed of massage motor 18 is controlled so that massage node 22 reciprocates in a rapid succession of short strokes to massage the body part. The bulk of shaft 20 moves up and down along reciprocating direction 46 according to the illustrated embodiment but it can be understood that a lateral component associated with the motion of eccentric connector 24 may be included.

Shaft 20 is affixed to massage node 22 using any of various conventional fastening means. Massage node 22 includes massage surface 50 which may be generally rounded or convex as shown in FIG. 1 and which may additionally or alternatively include undulations such as ridges 52 shown in FIG. 2. It should be understood that the shapes of massage node 22 and massage surface 50 shown in the figures are intended to be exemplary only and that various other shapes designed to comfortably massage the desired body part, may be used in other exemplary embodiments.

Now returning to FIG. 1, massage motor 18 is preferably electrically coupled to and controlled by massage motor control switch 26 or other variable setting massage motor control device. Massage motor control switch 26 is preferably located on handle portion 14 of housing 12 for easy access by the user. The speed of rotation of massage motor 18 is preferably manipulated by the user through massage motor control switch 26. In the preferred embodiment, massage motor control switch 26 includes various settings corresponding to various rotational speeds of massage motor 18 which, in turn, correspond to various reciprocating frequencies of massage node 22. Massage motor control switch 26 may include a microprocessor to achieve the multiple rotational speeds of massage motor 18. Massage motor 18 is internal to housing 12. According to the preferred embodiment in which massage motor 18 is an electrical motor, electricity may be provided by means of power cord 64. Other methods for powering massage motor 18, such as by using batteries retained within housing 12, may be used alternatively. Massage motor 18 may advantageously be controlled independently of other electronic features of the present invention.

In addition to exemplary massage motor 18 and the exemplary arrangement shown in FIGS. 1 and 2, various other means for causing massage node 22 to reciprocate thereby massaging a body part, may be used in other exemplary embodiments. The reciprocating motion of massage node 22 creates a percussion type of massaging by repeatedly and rapidly impacting the body part being massaged to sooth the area and relieve tightness and stress. According to other exemplary embodiments, a massage motor may be used which imparts a vibrational or other type of motion onto massage node 22 to massage the body part. According to yet another exemplary embodiment, multiple motors may be combined to produce a reciprocating or vibrating motion of massage node 22.

In the exemplary embodiment shown in FIG. 1, warm air massager 10 is designed so that the axis of handle portion 14 forms an acute angle with respect to reciprocating direction 46. More specifically, handle portion 14 axially forms an acute angle with respect to massaging direction 66 along which massage node 22 moves toward the body part being massaged. According to other exemplary embodiments, handle portion 14 may be oriented differently with respect to reciprocating direction 46. For example, handle portion 14 may include an axis which is generally parallel or perpendicular to reciprocating motion 46.

Another aspect of the present invention is the heated air which is provided to the body part being massaged through openings formed in the massage node. The means for facilitating the intake of ambient air into housing 12, heating the air and delivering the heated air to the body part being massaged, is also shown in FIG. 1. Fan 28 is driven by fan motor 30 which is preferably an electric motor connected to an electrical power source by means of power cord 64. According to one exemplary embodiment, fan 28 is a medium to high speed ducted propeller fan driven by electric fan motor 30. According to other exemplary embodiments, fan 28 may be a blower type fan or a slow, medium or high speed radial, axial or drum type fan. Fan motor 30 may be an AC or DC motor with the impeller/propeller of fan 28 attached directly to fan motor 30. Other fans and other methods for powering fan motor 30 may be used alternatively. According to one exemplary embodiment, fan motor 30 may be powered by other conventional sources such as batteries.

The speed of rotation of fan 28 is preferably controlled by a control device such as exemplary fan control switch 34 which is electrically coupled to fan motor 30. Fan control switch 34 may include a microprocessor and includes various settings corresponding to varying rotational speeds of fan 28, in the preferred embodiment. As the speed of fan 28 increases, so too does the rate of air intake and therefore the rate of heated air delivered to the body part being massaged since the airflow is contained within housing 12. Alternatively stated, the amount of heated air delivered to the body part being massaged, in time, increases with increased fan speed. Fan control switch 34 is preferably located on handle portion 14 for easy access by the user.

When fan motor 30 activates fan 28, ambient air from outside the housing is withdrawn into housing 12 through an opening such as intake vent 56 formed within housing 12. Intake ambient air flow is illustrated by arrow 48. In an exemplary embodiment, intake filter 32 may be included and positioned in various locations to filter the intake ambient air before it passes through heating element 36. Conventional filters may be used. In the exemplary embodiment, intake filter 32 is disposed within intake vent 56. Housing 12 is configured, and intake vent 56, fan 28, intake filter 32, and heating element 36 are arranged such that the intake ambient air withdrawn into housing 12 by means of fan 28, sequentially passes through intake vent 56 and intake filter 32 and is directed to traverse heating element 36 thereby becoming heated. As in the exemplary embodiment shown in FIG. 1, heating element 36 may be directly in line with fan 28 and fan motor 30. Heating element 36 may be mounted directly to fan motor 30 or it may be mounted separately and coupled to fan 28 and fan motor 30 via a rigid or flexible shaft, or other member. According to an exemplary embodiment, heating element 36 may be a resistive coil wire. According to another exemplary embodiment, heating element 36 may be a solid resistive heating element outfitted with a heat sink. Other conventional heating elements may be used alternatively and will be chosen to include a substantial surface area so that the air traversing the heating element is essentially completely heated upon passing through the heating element. The amount of heating is controlled so that the air is moderately heated to a comfortable temperature and the air directed to the body part being massaged is soothing and comfortable and not excessively hot and uncomfortable. In an exemplary embodiment, heating element 36 may be controlled by fan control switch 34 so that it operates when fan 28 operates. According to another exemplary embodiment, heating element 36 may be separately controlled and may be turned on and off by conventional switches or other control devices (not shown). Heating element 36 may include multiple settings for various degrees of heating and may be controlled by a control switch which may include a microprocessor to achieve multiple heat settings. Heating element 36 may also be controlled by a thermostat or other temperature regulating device. It should be understood that various other arrangements of the fan, fan motor and heating element may be used to withdraw air into the housing, heat the air and direct the heated air to the massage node.

Massage node 22 preferably includes at least one opening extending therethrough so that the heated air contained within housing 12 is directed by the force of fan 28 to exit warm air massager 10 through ports 40 formed on massage surface 50 of massage node 22. In this manner, heated air streams 54 are directly provided onto the user's body part being massaged. In the preferred embodiment, massage node 22 includes a plurality of openings extending therethrough and a plurality of ports 40. The internal flow of heated air within housing 12 is shown by internal air flow arrows 42. In an alternative embodiment, outlets 38 may additionally be formed in close proximity to massage node 22 for providing additional heated airflow to the body part being massaged. In the exemplary embodiment shown in FIG. 1, outlets 38 are formed adjacent massage node 22 within orifice 58 in which massage node 22 is situated. Stated alternatively, optional outlets 38 are formed between massage node 22 and housing 12, specifically, between massage node 22 and an edge of orifice 58. Optional outlets 38 which may be formed as shown in FIG. 1 or in other locations near massage node 22 are positioned to direct heated air toward or near the body part being massaged. In this manner, warm air is delivered, by means of heated air streams, directly to the body part being massaged.

It should be understood that ports 40 through which heated air streams 54 are directed, and which are disposed on massage surface 50 of massage node 22, are intended to be exemplary only. Ports 40 may be disposed at various locations on or adjacent to massage node 22 which itself may take on various shapes according to various exemplary embodiments. The size and number of ports 40 will vary depending on the amount of warm air desired. Ports 40 are preferably spaced apart on massage node 22 so that the heated delivered air is diffused as it is expelled from warm air massager 10 when directed to the body part being massaged. Ports 40 may take on various shapes such as narrow slits or circular openings. According to an exemplary embodiment, ports 40 provide a plurality of streams of heated air 54 to the body part at various angles with respect to the body part.

In the preferred embodiment, heated air is delivered to the body part being massaged concurrently with the massaging by massage node 22. According to other exemplary embodiments, the massager may be used without activating the heated air delivery feature or vice-versa. This is possible due to the separate control of the features by respective control switches massage motor control switch 26 and fan control switch 34. According to yet another exemplary embodiment, massage motor control switch 26 and fan control switch 34 may be commonly connected and the features operated simultaneously. According to still another exemplary embodiment, each of fan 28, motor 18, and heating element 36 may be commonly controlled by a single variable setting switch.

Figure 4:
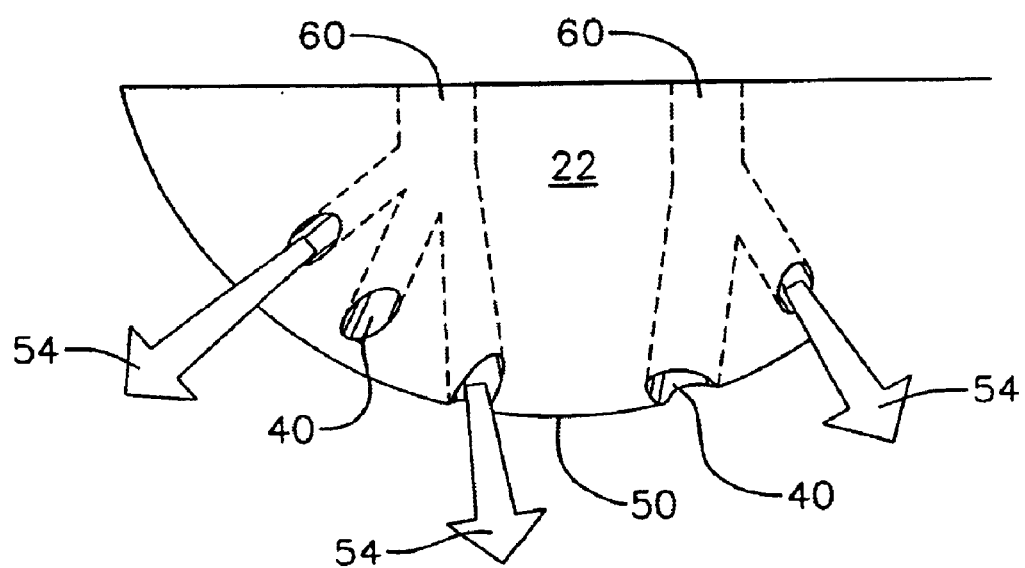
FIG. 4 is a side view of another exemplary embodiment of the massage node having openings therethrough and which includes outlet ports for directing heated air streams to the body part.

FIGS. 3 and 4 each illustrate side views of exemplary massage nodes 22. Massage node 22 includes at least one opening extending therethrough and terminating in at least one exemplary port 40 formed on massage surface 50 of massage node 22. Referring now to FIG. 3, a plurality of ports 40 are formed on massage surface 50. It should be understood that the rounded shape of massaging surface 50 is intended to be exemplary only. In the exemplary embodiment shown in FIG. 3, a plurality of conduits 60 are formed, each conduit corresponding to and terminating in a single port 40. Conduits 60 each extend through massage node 22.

According to another exemplary embodiment as shown in FIG. 4, the openings which extend through massage node 22 may be conduits 62 which are forked such that a single conduit terminates in multiple ports 40. In each of the embodiments shown in FIGS. 3 and 4, heated air streams 54 exit warm air massager 10 from corresponding ports 40 and are directed to the body part being massaged at various angles. According to another exemplary embodiment, each conduit such as conduits 60 shown on FIG. 3, may terminate in a single port and be angled with respect to other conduits unlike the essentially parallel conduits 60 shown in the exemplary embodiment of FIG. 3. According to yet another exemplary embodiment, each of heated air streams 54 may be directed to the body part at the same angle.

Figure 5:
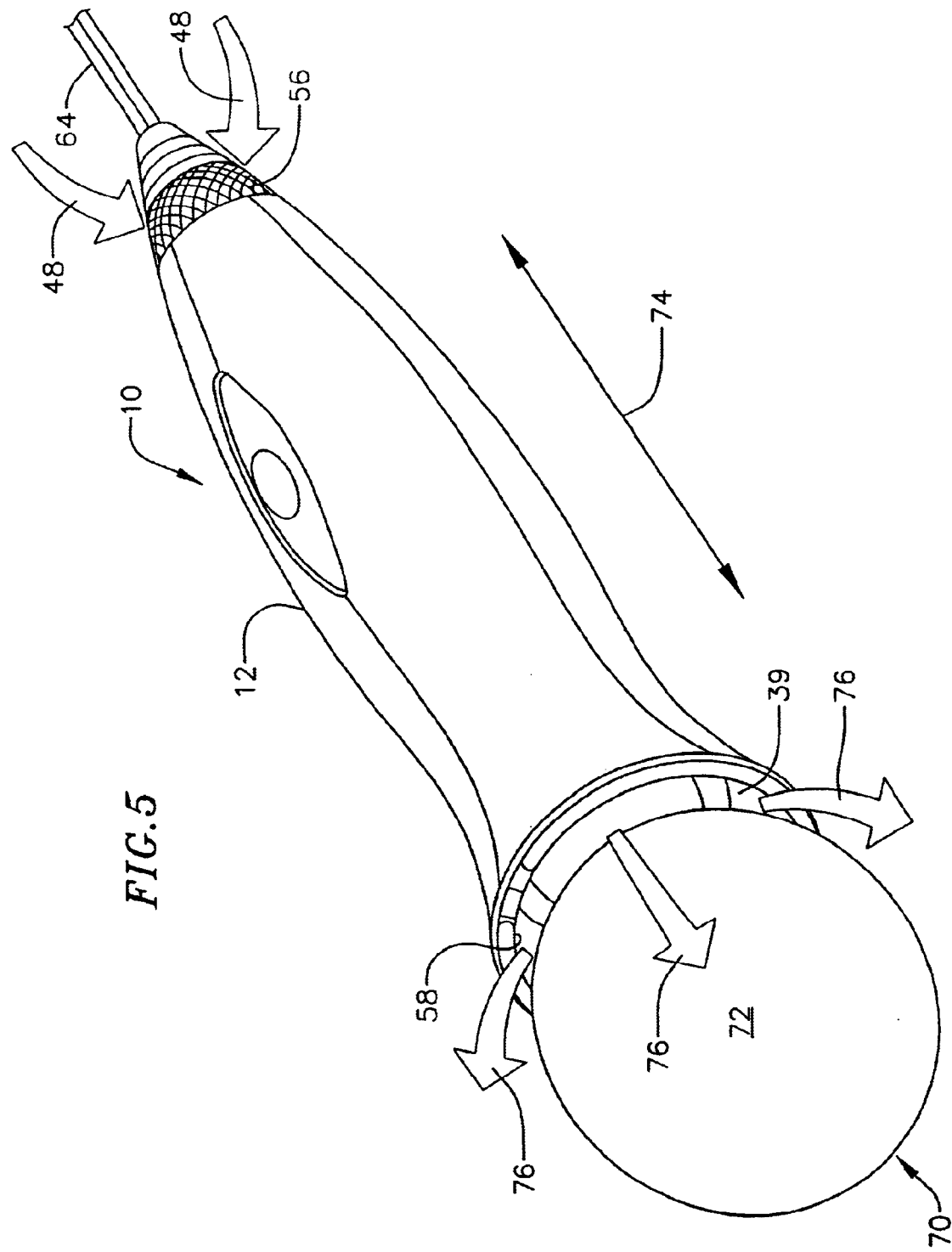
FIG. 5 is perspective view of another exemplary embodiment of the warm air massager.

FIG. 5 shows another exemplary embodiment of the warm air massager in which housing 12 is generally cylindrical in shape. The generally cylindrical shape of housing 12 may advantageously include contours to accommodate the housing being held by the user. According to an exemplary embodiment, cylindrical housing 12 may include air intake vent 56 on one end of the cylinder and an opening such as exemplary orifice 58 at the opposite end of the cylinder of housing 12. Warm air massager 10 includes means for facilitating the withdrawal of ambient air 48 from without housing 12, through intake vent 56 and into housing 12, and means for heating the ambient air to produce heated air streams 76, which are directed through outlet 39 of orifice 58 and also through various other outlet ports (not shown) according to other exemplary embodiments. Heated air streams 76 are directed towards the user's body part being massaged. In the exemplary embodiment shown, massage node 70—a ball in the illustrated embodiment, extends axially from orifice 58 and heated air streams 76 are directed through outlet 39, around ball 70 and towards the user's body part being massaged. In the exemplary embodiment shown, outlet 39 may extend circumferentially around massage node 70, within orifice 58. According to other exemplary embodiments, other shapes including other round or ellipsoid members, may be used as massage node 70. Massage node 70 includes convex massage surface 72. Massage surface 72 of massage node 70 may be formed of materials such as described in conjunction with the other exemplary embodiments. According to another exemplary embodiment, massage surface 72 of massage node 70 may advantageously include outlet ports (shown in FIGS. 1, 3 and 4) through which additional streams of heated air are directed towards the user's body part.

Warm air massager 10 includes means for causing massage node 70 to vibrate and/or reciprocate. According to an exemplary embodiment, massage node 70 may reciprocate axially along a direction generally parallel to axial direction 74.

According to a preferred embodiment, massage node 70 may include a motor (not shown) therein. According to an exemplary embodiment, the motor contained within massage node 70 may be a rotary motor. The motor may be capable of causing massage node 70 to vibrate and/or reciprocate. According to another exemplary embodiment, an additional motor may be included within housing 12. Such an additional motor (not shown) is housed substantially within housing 12 and causes massage node 70 to vibrate or reciprocate independently of any motion induced by the motor housed substantially within massage node 70. The motors may be separately controllable. The motor arrangement including a first motor substantially housed within massage node 70, a second motor substantially housed within housing 12, and the arrangement including both motors, is described in U.S. Pat. No. 5,925,002, entitled HAND-HELD VIBRATORY MASSAGER, filed on Sep. 22, 1995, the contents of which are herein incorporated by reference. According to an exemplary embodiment, the additional motor contained within housing 12 may be substantially similar to the motor described in conjunction with the embodiment shown in FIGS. 1 and 2, but will be configured to provide a reciprocating motion of massage node 70 along a generally axial direction such as axial direction 74.

As described in conjunction with the other embodiments, the motor or motors and the means for delivering heated streams of air, may each be separately controlled. According to other exemplary embodiments, housing 12 may take on other shapes, massage node 70 may take on other shapes and may be positioned differently within orifice 58 which may also take on various shapes. Furthermore, the type and position of the motor or motors within massage node 70 and within housing 12, may be varied according to various exemplary embodiments.

The present invention has been described with respect to a hand-held percussion-type massager. It should be understood that such is by way of example only. The present invention provides a heated air stream directed through at least one opening formed in a massage node and delivered to a body part being massaged. This novel feature can be equally applied to various other types of massagers such as stationary massagers, massaging chairs, massage tables and other similar massaging equipment. This aspect of the present invention may be applied to massagers dedicated to being foot massagers, neck massagers, back massagers, and other massaging devices. The configurations of the various elements described may also be varied within the scope of the present invention. Similarly, the means for facilitating the intake of ambient air into the housing and for heating the air and delivering the air through the massage node, may also be modified within the scope and spirit of the present invention. According to various embodiments, the warm air massager may not be enclosed within a housing and alternative means used to direct heated air streams through the massage node and to the body part being massaged. Furthermore, the means for providing motion such as vibration or reciprocation of the massage node may be varied within the scope and spirit of the present invention. The above description therefore should not be construed as limiting the present invention but merely as an exemplification of exemplary embodiments thereof. Those skilled in the art will envision further modifications within the scope and spirit of the present invention as defined by the appended claims.

What is claimed is:

1. A warm air massager for heating and impassaging a body part, comprising: a housing having a handle portion and a massaging portion, the housing having an orifice adjacent the massaging portion of the housing; a massage node situated in the orifice and extending outwardly from the orifice, the massage node having a plurality of openings extending therethrough; means for causing said massage node to reciprocate for massaging a body part with a percussion-type massage; and means for delivering heated air through said orifice in the housing and plurality of openings in the massage node at a plurality of angles with respect to said body part, when said warm air massager is in fixed position with respect to said body part.

2. The warm air massager as in claim 1, in which said means for delivering heated air further comprises means for delivering said heated air to said body part through at least one outlet formed in said housing, and between said massage node and an edge of said orifice.

3. The warm air massager as in claim 1, in which said means for causing said massage node to reciprocate includes a massage motor internal to said housing.

4. The warm air massager as in claim 1, wherein said massage node is capable of motion along a massaging direction toward said body part and said handle portion includes an axis which forms an acute angle with said massaging direction.

5. The warm air massager as in claim 1, in which said means for delivering heated air includes a fan.

6. The warm air massager as in claim 5, in which said fan comprises one of a medium to high speed ducted propeller fan, a radial fan, and an axial fan.

7. The warm air massager as in claim 5, in which said fan is controllable by a control device having various settings corresponding to various fan speeds.

8. The warm air massager as in claim 1, in which said means for delivering heated air through said plurality of openings of said massage node includes means for drawing ambient air into said housing and a heating element for heating said ambient air inside said housing to produce said heated air.

9. The warm air massager as in claim 8, in which said means for drawing ambient air into said housing includes a fan and said fan and said heating element are separately controllable.

10. The warm air massager as in claim 8, further comprising a filter for filtering said ambient air before said ambient air is heated.

11. The warm air massager as in claim 8, wherein said heating element comprises a resistive coil wire.

12. The warm air massager as in claim 8, wherein said heating element comprises a solid resistive heater outfitted with a heat sink.

13. The warm air massager as in claim 8, in which said means for drawing ambient air into said housing includes a fan, a fan motor, and a fan control switch electrically coupled to said fan motor for controlling rotational speed of said fan.

14. The warm air massager as in claim 8, in which said housing includes an intake vent and said means for drawing ambient air into said housing includes withdrawing said ambient air from outside of said housing and into said housing through said intake vent.

15. The warm air massager as in claim 8, wherein said means for drawing ambient air into said housing comprises a fan and a fan motor and said fan directs said intake ambient air to traverse said heating element.

16. The warm air massager as in claim 15, wherein said means for causing said massage node to reciprocate includes a massage motor, and said fan motor and said massage motor are separately controllable.

17. The warm air massager as in claim 1, wherein said means for delivering heated air includes means for directing a plurality of streams of heated air to said body part at a plurality of angles with respect to one another.

18. The warm air massager as in claim 1, wherein each of said plurality of openings extends to at least one port formed on a massaging surface of said massage node.

19. The warm air massager as in claim 1, in which said means for causing said massage node to reciprocate includes a massage motor coupled to said massage node by means of a shaft.

20. The warm air massager as in claim 19, in which said shaft is fixedly coupled to said massage node and thereby reciprocates along with said massage node and said massage motor provides rotational motion and an eccentric connector couples said massage motor to said shaft and causes said shaft to reciprocate substantially axially.

21. The warm air massager as in claim 1, in which said means for causing said massage node to reciprocate includes a massage motor having a massage motor control device including various settings corresponding to various reciprocating frequencies.

22. The warm air massager as in claim 1, wherein said warm air massager is a hand held unit.

23. The warm air massager as in claim 1, wherein said massage node includes a massaging surface for massaging said body part and said massaging surface includes undulations formed therein.

24. The warm air massager as in claim 1, wherein said massage node includes a convex massaging surface for massaging said body part.

25. The warm air massager as in claim 2, in which said means for causing said massage node to reciprocate includes a massage motor controlled by a control switch disposed on said handle portion, and said means for delivering said heated air includes a fan controlled by a further control switch further disposed on said handle portion.

26. A warm air massager for heating and massaging a body part, comprising: a housing having a handle portion and a massaging portion, the housing having an orifice adjacent the massaging portion of the housing; a massage node situated in the orifice and extending outwardly from the orifice, the massage node having a plurality of openings extending therethrough; means for causing said massage node to vibrate for massaging a body part with a percussion-type massage; and, means for delivering heated air through said orifice and said plurality of openings at a plurality of angles with respect to said body part, when said warm air massager is in fixed position with respect to said body part.

27. A warm air massager for heating and massaging a body part, comprising:
a housing having a handle portion and a massaging portion, the housing further including an orifice adjacent the massaging portion of the handle;
a massage motor disposed within said housing;
a shaft driven by said message motor to repeatedly reciprocate;
a massage node extending outwardly from the orifice in the housing and coupled to said shaft such that said massage node reciprocates along with said shaft thereby massaging said body part with a percussion-type massage, the massage node including a plurality of openings extending therethrough;
a fan motor enclosed within said housing, said fan motor and said massage motor being separately controllable;
a fan coupled to and driven by said fan motor to draw ambient air from without said housing, into said housing;
a heating element provided between said fan and said massage node and capable of heating said ambient intake air and producing warm exhaust air; and
said fan being further capable of delivering a plurality of streams of said warm exhaust air through said orifice and said plurality of openings and to a body part being massaged, at a plurality of angles with respect to each other.

28. A method for massaging and heating a body part comprising:
providing a massage node adapted for massaging a body part;
causing said massage node to reciprocate toward and away from said body part for providing a percussion-type massage; and
directing a plurality of streams of heated air through said massage node and adjacent said massage node toward said body part at a plurality of angles with respect to said body part, when in fixed position with respect to said body part.

29. The method as in claim 28, further comprising directing at least one further stream of heated air towards said body part, but not through said massage node.

30. The method as in claim 28, further comprising providing a housing including an orifice, said massage node extending from said orifice, and further comprising withdrawing ambient air from outside said housing and heating said ambient air within said housing to produce said heated air.

31. The method as in claim 28, in which said heating includes said fan causing said ambient air to traverse a resistive coil wire heating element.

32. The method as in claim 28, in which said directing comprises directing said plurality of streams of heated air through a corresponding plurality of ports formed on a massage surface of said massage node.

33. A warm air massager for heating and massaging a body part, comprising:
a massage node having a plurality of openings extending therethrough;
means for causing said massage node to reciprocate for massaging a body part with a percussion-type massage; and,
means for delivering a plurality of streams of heated air through said massage node and adjacent said massage node at a plurality of angles with respect to one another and toward said body part.

34. The warm air massager as in claim 33, wherein said massage node has a massage surface including a plurality of ports terminating thereon and said means for delivering a plurality of streams of heated air includes delivering said plurality of streams from said plurality of ports.

35. A warm air massager for heating and massaging a body part, comprising: a housing having a handle portion and a massaging portion, the housing further including an orifice adjacent the massaging portion of the handle; a massage node extending from the orifice and having a plurality of openings extending therethrough; means for causing said massage node to reciprocate for massaging a body part with a percussion-type massage; and, means for simultaneously delivering heated air through said orifice and said plurality of openings at a plurality of angles with respect to said body part.

* * * * *

UNITED STATES PATENT AND TRADEMARK OFFICE
CERTIFICATE OF CORRECTION

PATENT NO. : 6,786,878 B2
DATED : September 7, 2004
INVENTOR(S) : Hans Dehli

It is certified that error appears in the above-identified patent and that said Letters Patent is hereby corrected as shown below:

Drawings,
FIG. 4, Sheet 2 of 3, delete character references numbers "60", insert -- 62 --

Title page,
Item [56], References Cited, U.S. PATENT DOCUMENTS, insert the following:
--1,534,444 04/1925 Feldheym
1,782,005 11/1930 Grison
1,844,247 02/1932 Freemon
1,955,863 04/1934 Schmidt...174/173
2,097,455 11/1937 Fisher......128/24.2
2,154,428 04/1939 Andres.....219/21
2,582,617 01/1952 August.....128/24.1
3,370,583 02/1968 Teranishi..128/24.1
3,413,973 12/1968 Teranishi..128/24.2
3,467,080 09/1969 McNair.....128/24.2
3,481,326 12/1969 Schamblin.128/24.2
3,503,395 03/1970 Meyer.......128/24.2
4,722,326 02/1988 Ruderian...128/24.1
4,566,442 01/1986 Mabuchi, et al..128/52
5,925,002 07/1999 Wollman....601/70--

Column 8,
Line 17, delete "impassaging" insert -- massaging --

Signed and Sealed this

Fourth Day of January, 2005

JON W. DUDAS
*Director of the United States Patent and Trademark Office*